United States Patent
Gould et al.

(10) Patent No.: US 8,452,548 B2
(45) Date of Patent: May 28, 2013

(54) BASE OIL LOW TEMPERATURE PROPERTY CLASSIFICATION MODEL

(75) Inventors: Ronald M. Gould, Sewell, NJ (US); Eugine Choi, Marlton, NJ (US)

(73) Assignee: Exxonmobil Research and Engineering Company, Annandale, NJ (US)

( * ) Notice: Subject to any disclaimer, the term of this patent is extended or adjusted under 35 U.S.C. 154(b) by 357 days.

(21) Appl. No.: 12/584,526

(22) Filed: Sep. 8, 2009

(65) Prior Publication Data

US 2010/0070202 A1    Mar. 18, 2010

Related U.S. Application Data

(60) Provisional application No. 61/191,898, filed on Sep. 12, 2008.

(51) Int. Cl.
    *G01N 31/00* (2006.01)
(52) U.S. Cl.
    USPC .................................. 702/30; 702/27; 702/32
(58) Field of Classification Search
    USPC ............................................. 702/30, 22–23
    See application file for complete search history.

(56) References Cited

U.S. PATENT DOCUMENTS

| | | | |
|---|---|---|---|
| 4,839,074 A * | 6/1989 | Rossi et al. .................... | 508/467 |
| 6,295,485 B1 | 9/2001 | Gleeson et al. | |
| 6,317,654 B1 | 11/2001 | Gleeson et al. | |
| 6,720,293 B2 * | 4/2004 | Bovington et al. ........... | 508/192 |
| 2005/0003974 A1 * | 1/2005 | Briggs et al. .................. | 508/591 |
| 2006/0122079 A1 * | 6/2006 | Kaneshige et al. ........... | 508/591 |
| 2007/0254821 A1 * | 11/2007 | Aguilar et al. ................ | 508/555 |

FOREIGN PATENT DOCUMENTS

JP    1994288944 A    10/1994

OTHER PUBLICATIONS

P. Redelius, "The Use of DSC in Predicting Low Temperature Behavior of Mineral Oil Products", *Thermochimica Acta*, 85 (1985), pp. 327-330.
F. Noel, "Thermal Analysis of Lubricating Oils", *Thermochimica Acta*, 4 (1972), pp. 377-392.
Z. Jiang, et al., "Measurement of the wax appearance temperatures of crude oils by temperature modulated differential scanning calorimetry", *Fuel*, 80 (2001), pp. 367-371.
P. Claudy, et al., "Crude oils and their distillates: characterization by differential scanning calorimetry", *Fuel*, 1988, vol. 67, pp. 58-61.
P. Claudy, et al., "Diesel fuels: determination of onset crystallization temperature, pour point and filter plugging point by differential scanning calorimetry. Correlation with standard test methods", *Fuel*, 1986, vol. 65, June, pp. 861-864.
F. Pochetti, et al., "Determination of Paraffin (Waxes) in Mineral Oils by Differential Calorimetry", *Riv Combust*, V23, N. 10, Oct. 1969, pp. 496-500.

(Continued)

*Primary Examiner* — Mischita Henson
(74) *Attorney, Agent, or Firm* — Robert A. Migliorni

(57) ABSTRACT

In one embodiment a method to determine at least one low temperature property of the lubricant oil is disclosed. This method comprises obtaining a base stock, generating a DSC curve of wax versus temperature using a heating curve for the base stock, correlating the heating curve of the base stock with a MRV for a formulated oil, and determining the MRV of the lubricant oil from the correlation of the base stock to the MRV of the corresponding desired base oil.

2 Claims, 4 Drawing Sheets

OTHER PUBLICATIONS

C. Giavarini, et al., "Behavior of Lubricating Oils at Low Temperatures", *Riv Combust*, V 23, N. 9, Sep. 1969), pp. 448-453.

D. Tiwary, et al., Phase transformation and rheological behaviour of highly paraffinic "waxy" mixtures, *Canadian Journal of Chemical Engineering*, 82/1, Feb. 2004, pp. 162-174.

C. Vecchi, et al., "Evaluation of the Low-Temperature Behavior of Petroleum Middle Distillates by Differential (Scanning) Calorimetry", Natl Anal Chem Congr (Ferrara 10/16-18/73) *Riv Combust* V27, N. 11-12, 512-518, Nov.-Dec. 1973.

M. A. Vickars, et al., "The Development of European Test Methods for the Measurement of Engine Oil Viscosities at Low Temperatures", ASTM Special Technical Publication 1992, No. 1143, Dec. 10, 1991, pp. 81-95.

ASTM Standard D4684-07: "Standard Test Method for Determination of Yield Stress and Apparent Viscosity of Engine Oils at Low Temperature", V. 5.02, Mar. 1, 2007, pp. 649-661.

J. F. Guzauskas, "Characteristics of wax extracted from lubricant basestocks", *Lubrication Engineering*, vol. 50, 4, pp. 326-336.

O. I. Matveeva, et al., "Estimation of low-temperature properties of semisolid lubricant dispersion media", *Khimiya I. Tekhnologiya Topliv I Masel*, Sep. 1991, No. 9, pp. 35-37.

* cited by examiner

BASE OIL LOW TEMPERATURE PROPERTY CLASSIFICATION MODEL

CROSS-REFERENCE TO RELATED APPLICATION(S)

Non Provisional Application based on U.S. Ser. No. 61/191,898 filed Sep. 12, 2008.

BACKGROUND

Compositionally-based tools have been used to pre-select economically viable crude oils for lube refinery test runs and subsequent product quality evaluations for many years. These tools require detailed compositional characterization of a wide range of fuels and lubes crude assays to support their use. An integrated lubes process model incorporates fundamental models for distillation, lube extraction, dewaxing, and hydroprocessing and determines estimated yields and compositions of base oils from crude assays. The thermal and oxidation stability of finished products formulated from those base oils is then rapidly assessed by a set of compositionally-based lubes product quality models. The product quality models can be either embedded within lube process models or used in standalone mode.

Once a crude is screened using these tools, a refinery will typically conduct a test run to confirm process yields and to obtain product for quality assurance ("QA") testing. The main focus of the product testing is to determine low temperature performance, interfacial behavior, and any other properties of the base oils which, when blended into the QA formulations, cannot be determined by existing models.

Clearly, the potential of the compositional-based approach was being limited by the absence of a predictive low temperature property ("LTP") tool. Accordingly, there is a need for a predicative low temperature property tool. This invention satisfies that need.

SUMMARY

In one embodiment a method to determine at least one low temperature property of the lubricant oil is disclosed. This method comprises obtaining a base stock, determining the residual wax distribution of that base stock as a function of temperature using Differential Scanning Calorimetry (DSC), then using that residual wax distribution to determine, for example, the MRV (ASTM D-4684) of a fully formulated lubricant oil based upon prior empirical correlation of the base stock DSC results to the MRV of the corresponding desired base oil.

DETAILED DESCRIPTION

We have developed a low-temperature property predictive tool which, in one embodiment, can be integrated with a lubes crude compositional data base, a proprietary lubes refining process model, and a set of product quality control models to adequately project fully formulated lube product performance and base oil production economics. The process model uses the compositional data for a candidate crude oil mixture to determine the distillation, extraction, dewaxing, and hydroprocessing unit operating conditions required to make a fit-for-purpose base oil from the candidate crude oil mixture. The lube product quality models then use key compositional and physical property parameters of the base oils so produced to determine if the fully formulated lube product, and by inference the corresponding crude mixture, is appropriate for a desired use. In another embodiment, this novel tool enables selection of candidate crude oils base stock manufacture without the need for subsequent refinery test run when specified criteria are met. The tool leverages an assay data base with preexisting models. This tool is based on residual wax distribution data measured by Differential Scanning Calorimetry (DSC). The tool uses the wax distribution to determine whether or not the corresponding fully formulated lubricant product, for example, a 10W-40 or a 20W-50 automotive engine oil will pass MRV yield stress and apparent viscosity specifications. It would then be obvious to one skilled in the art that any set of fully formulated lube products whose MRV performance criteria are less stringent than those of the QA formulations would also be protected by the tool.

The LTP tool can reduce significantly the time required to assess the potential of lubricant products produced from any given candidate crude mixture. While refinery field testing can require many months to complete, candidate crude assessment can be reduced in many instances to less than a day provided an acceptable crude compositional assay is available. This compositionally-based protocol will enable the selection of the lube crude feed mix to be tailored to a given refinery's specific process scheme and product property specification set. The low temperature property tool uses commercially available Differential Scanning Calorimetry (DSC) technology to determine both the total amount of residual wax as well as the distribution of residual wax as a function of temperature in a base oil sample after solvent or catalytic dewaxing. The wax content and distribution have been empirically correlated to key low temperature properties, specifically those measured by the Mini-Rotary Viscometer (MRV; ASTM D-4684).

A detailed description of the MRV test can be found in ASTM document D-4684. The target evaluation temperature is a function of the finished product specification.

Figure 1:
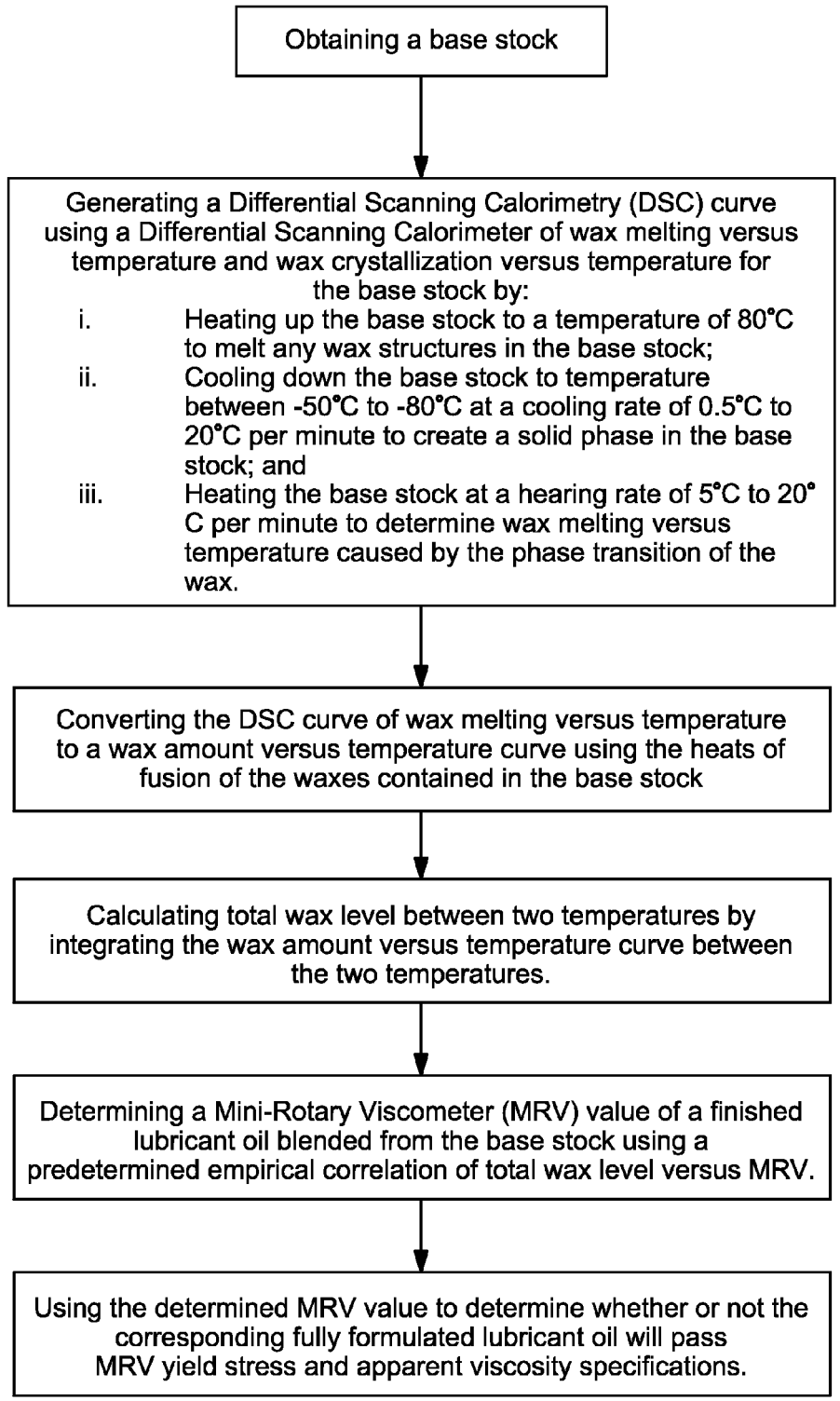
FIG. 1 is a flow chart of an embodiment of the invention.

In one embodiment, the prediction of whether the MRV meets performance requirements comprises three steps. These steps are shown schematically in FIG. 1. In Step 1, a DSC trace consisting of a measurement of the energy required during both wax crystallization and wax dissolution versus temperature is generated for base oil. In Step 2, calculate the residual wax distribution for base oil from the base oil heating curve using a pre-developed correlation. In Step 3, determine the low temperature properties of the desired formulation based on the base oil wax distribution.

We have developed two separate correlation sets using this embodiment. The first correlation set maps DSC results for 150N base oils to MRV apparent viscosity measured for a proprietary 10W-40 automotive engine oil Quality Assurance formulation. The second maps DSC results for 600N base oils to the MRV yield stress and MRV apparent viscosity measured for a proprietary 20W-50 automotive engine oil Quality Assurance formulation. Additional correlations in the future may be developed as necessary to obtain favorable results.

The low temperature correlations described above were developed in straightforward fashion by first selecting a set of representative base oils having a wide range and distribution of residual waxes. Some base oil samples were intentionally augmented with residual wax dopants where the natural level or distribution of residual wax was not sufficient to induce a low temperature property failure. A low property failure is when the MRV does not meet the accepted level for the given formulation. The accepted MRV level is a function of the desired finished formulation.

The DSC cooling and heating curves for these samples were then determined. The DSC cooling and heating curves are heat flow as a function of temperature. The DSC curve is determined by first heating the base oil sample to a temperature sufficient to melt all the residual wax contained in the base oil. The measurement is typically preferably 80° C. but can vary based on the base stock. Preferably, a temperature should be chosen so that all the residual wax is melted. The sample is then cooled at a cooling rate of 0.5° C. to 20° C. per minute and preferably 1 to 10° C. per minute and in the examples in the application it was 3° C. per minute. The base oil is cooled to a temperature sufficient to completely solidify the base oil sample. For most base oil samples, this will be between −50 to −80° C.

The DSC heating curve is then created by heating at a rate of approximately 5 to 20° C. and preferably 10° C. per minute. Preferably, the cooling and heating rates should be kept consistent to keep the correlation accurate. This was done with a commercially available DSC unit but any equivalent machine could be used.

In one embodiment, a correlation can be developed between the cumulative heat flow or energy absorbed by the sample and the measured MRV of the finished lubricant. In this embodiment, this correlation is made by determining the amount of energy absorbed between two specified temperatures for example −30° C. and the pour point of the base oil which typically ranges from −9 to −18° C. but can range considerably based on the low temperature properties of base stock. A person skilled in the art will recognize many methods to determine accurately the heat flow measurements obtained by DSC including for example, compensating for baseline drift via numerical and graphical methods.

The DSC data can be converted from an absorbed energy to a wax amount by using the heat of fusion of the waxes contained in the sample. The heat of fusion is the amount of energy needed to induce a phase change in the wax. The amount of wax is typically determined for temperatures between the cloud point and a pre-selected temperature below the cloud point.

The corresponding total wax level and distribution are calculated as a function of temperature for each base oil sample using experimentally determined heats of formation for petroleum-derived waxes. Alternatively, the corresponding total wax level and distribution can be determined by using heats of formation obtained from the literature. The results are then correlated against experimentally measured MRV apparent viscosity and/or yield stress values in selected automotive engine oil formulations. The formulations selected are preferentially those with relatively weak additive packages, especially in the area of low temperature performance. This preferred approach enables one or a small number of low temperature Quality Assurance formulations with weak additive packages to protect a broad range of commercially applicable formulations without the need for extensive testing.

In one embodiment, this model can be used as part of an overall compositionally-based lube feed approval protocol ("CLFAP"). A description of the preexisting components is provided below.

The first step in the CLFAP is to ensure that the candidate crude oil is economically attractive for lubes manufacturing. A viable candidate crude oil would have an assay, based on a combination of physical property and compositional measurements. Measurements can be obtained by a variety of methods or combination of methods including but not limited to Fourier Transform Infrared (FTIR) analysis, or mass spectroscopy, and/or gas chromatography, that is sufficiently accurate and detailed to support this protocol. The candidate crude should be available in commercially viable quantities and have sufficiently consistent properties to justify the effort and expense of the approval process. In addition, the crude should come from a reliable crude oil producer and be competitively priced relative to its integrated product value. Determination of crude oil economics is a joint effort that can involve crude traders, refinery optimizers, and refinery coordinators. Candidate crude oils are first identified by the traders; then an economic model is run by the refinery to evaluate the overall profitability of the candidate crude.

The economic model includes by definition a sufficiently detailed process operations model to enable the determination of key operating conditions and product yields for each of the process steps used in manufacturing the base oil. These would include but are not limited to distillation, extraction, hydroprocessing, and solvent and/or catalytic dewaxing.

EXAMPLE

In this example embodiment, the process is applied to Group I base oil manufacture. An individual skilled in the art could apply the same approach for the approval of crude oils for either Group II or Group III base oil manufacture. Potential feed components include but are not limited to traditional paraffinic and naphthenic-type crude oils; acidic crudes, defined as those having a total acid number above 1.5 mg KOH/g; condensates; hydrocrackates; residual feeds; and synthetic crude oils with or without commingled bitumen.

Generally, the candidate crude is part of a mixture of crude oils being fed to the lube production train at any given time. The candidate crude can be evaluated in context by using either the real-time crude mix being run at each refinery or a pre-selected companion crude slate typical of average refinery operation. Once the crude mix is determined, process operating conditions, product yields, base oil qualities, and base oil composition are determined by the lube process model. The process model tracks molecular composition from the crude feed mix through the individual process operations to the base stock. Such a model is comprised of a number of sub-models through which the composition must flow. The detailed compositional information about the crude oils being utilized by the process model resides in the crude assay database.

If the candidate crude is found to be attractive economically, the next step is to determine if finished lubricant made from the candidate crude will meet all applicable performance specifications. This is accomplished by using the base oil compositions determined in the process model in the product quality model. The intent of the specifications within the model is to constrain the base oil composition to a range that has demonstrated acceptable performance. A low risk classification indicates that the base oil being evaluated is similar in composition to base oils that have historically performed well with the appropriate additive systems. A high risk classification indicates that the base oil is similar in composition to stocks that either have demonstrated poor performance in one or more finished products or were substantially different compositionally from previously approved stocks.

The commercially demonstrated tools and procedures described above are used to qualify crude oils for lubes manufacture in all areas with the exception of low temperature properties. The present invention addresses this gap. The development of such a low temperature property (LTP) model will therefore enable a substantial reduction in approval time since a plant test and subsequent product quality testing would not be required.

The LTP model uses Differential Scanning Calorimetry (DSC) to quantify the wax distribution as a function of temperature for the base oils, base oil/wax mixtures, and finished oils. DSC has also been used successfully to predict pour point and cloud point of base oils (1), but has not been applied previously to the prediction of low temperature properties of finished lubes.

The use of this technique unexpectedly determined that acceptable low temperature properties for base oils can be defined by DSC to provide satisfactory low temperature performance for finished lubes blended from those base oils.

The finished product formulations used to generate the data used to develop the LTP model are detailed in Table 1 and were:
Engine Oil A 10W-40: for 150N
Engine Oil B 10W-40: for 150N
Engine Oil C 20W-50: for 600N.

TABLE 1

Group I Quality Assurance Monitoring Formulations

|  | Engine Oil A 10W40 | Engine Oil B 10W-40 | Engine Oil C 20W-50 |
|---|---|---|---|
| Base oil blend with 150N test base oils | 79.3 | 80.0 | — |
| Base oil blend with 600N test base oil | — | — | 82.8 |
| Detergent inhibitor package and viscosity index improver | 20.5 | 19.8 | 16.9 |
| Pour point depressant A | 0.2 | — | — |
| Pour point depressant B | — | 0.2 | — |
| Pour point depressant C | — | — | 0.3 |
| Total | 100.0 | 100.0 | 100.0 |
| MRV app. visc limit, cP | 53,400 | 53,400 | 55,600 |

The formulations in Table 1 are considered to be the limiting formulations from a low temperature properties (LTP) perspective for a defined set of additive technologies. The MRV is the critical LTP test for all three products.

In one embodiment, to predict whether the MRV will be passing or failing, a differential scanning calorimeter is used to first cool the sample, then to generate a heating curve for a given base oil sample. That heating curve is then integrated so that the total heat flow based on wax melting is determined as a function of temperature. The instantaneous and integrated heat flows provide a quantitative indication of total wax content and wax distribution. The preferred method of obtaining this integral is to manually employ standard graphical analysis tools embedded in the DSC software. This approach provides for superior identification of the glass transition temperature and compensation of baseline signal drift, both of which must be accounted for in the analysis to achieve the desired level of accuracy. The integrated heat flow from the melting curve can then be correlated to the critical MRV properties.

In another embodiment, the heating curve can be translated to the amount of wax and then correlated to the critical MRV properties. A first-principles translation of the heating curve to the physical amount of wax corresponding to these phase changes requires detailed knowledge of the sample composition and the corresponding heats of fusion for each molecular species. Since no accurate, fundamentally-based model existed at the time of this work, it was decided to use an empirical correlation relating the wax content of representative, commercially produced lube base stocks to DSC heat input as a function of temperature to calculate the wax distribution versus temperature of test samples from their experimentally measured heating curves. A person skilled in the art with the benefit of this disclosure could create a new fundamentally-based model for this application. The operative equation is:

$$DW(T2-T1) = DH(T2-T1) / \{1.731 \times [T1 + ((T2-T1)/2)] + 141.5\} \quad \text{Eq. 1}$$

where:
DW(T2-T1)=Fraction of total wax melted between Time 1 "T1" and Time 2 "T2"
DH(T2-T1)=Heat absorbed between T1 and T2, J/g
Ti=Temperature, ° C.

TABLE 2

Wax distribution comparison for base oils from 2 different crudes

|  | Crude A | Crude B |
|---|---|---|
| DSC wax at −50° C., wt % | 17.7 | 15.8 |
| DSC wax at −10° C., wt % | 1.0 | 3.6 |
| DSC wax at −5° C., wt % | 0.1 | 2.0 |
| MRV apparent vis at −20° C., cP | 21,200 | 73,600 |
| MRV yield stress −20° C., Pa | <35 | 245 < YS < 280 |

Table 2 shows the difference in wax distribution for base oils produced from 2 different crudes. The MRV of the finished oil using base oil from Crude A meets performance specifications while the MRV of the finished oil using base oil from Crude B do not. This occurs because the DSC wax distribution of the dewaxed oil from Crude A indicates a lower concentration of molecules of highly paraffinic nature, such as a small number of short branches or a long, uninterrupted backbone, at higher temperatures compared to the Crude B derived base oil.

Table 3 lists the MRV yield stress and apparent viscosities at −20° C. for a series of 600N base stocks used in the 20W-50 formulation. Table 3 also lists the corresponding DSC data of the base oils.

TABLE 3

| Base stock | DSC wax at −30 C. wt % | DSC wax at −25 C. wt % | DSC wax at −20 C. wt % | DSC wax at −15 C. wt % | DSC wax at −10 C. wt % | DSC wax at −5 C. wt % | DSC wax at 0 C. wt % | MRV yield stress at −20° C., Pa | MRV apparent visc at −20° C., cP |
|---|---|---|---|---|---|---|---|---|---|
| 1 | 11.4 | 9.1 | 6.3 | 3.4 | 1.0 | 0.1 | 0.0 | 35 | 21179 |
| 2 | 8.4 | 6.5 | 4.3 | 2.1 | 0.4 | 0.1 | 0.0 | 35 | 18677 |
| 3 | 8.1 | 6.7 | 5.0 | 3.3 | 1.7 | 0.5 | 0.1 | 35 | 25488 |
| 4 | 9.4 | 8.0 | 6.2 | 4.4 | 2.7 | 1.2 | 0.2 | 70 | 38741 |
| 5 | 10.4 | 9.0 | 7.2 | 5.4 | 3.6 | 2.0 | 0.6 | 280 | 73640 |

TABLE 3-continued

| Base stock | DSC wax at −30 C. wt % | DSC wax at −25 C. wt % | DSC wax at −20 C. wt % | DSC wax at −15 C. wt % | DSC wax at −10 C. wt % | DSC wax at −5 C. wt % | DSC wax at 0 C. wt % | MRV yield stress at −20° C., Pa | MRV apparent visc at −20° C., cP |
|---|---|---|---|---|---|---|---|---|---|
| 6 | 9.2 | 7.8 | 6.0 | 4.3 | 2.6 | 1.1 | 0.2 | 35 | 30156 |
| 7 | 8.8 | 7.5 | 5.9 | 4.3 | 2.7 | 1.3 | 0.3 | 70 | 36097 |
| 8 | 8.7 | 7.2 | 5.6 | 3.9 | 2.4 | 1.1 | 0.2 | 35 | 31452 |
| 9 | 8.2 | 6.8 | 5.1 | 3.5 | 1.9 | 0.6 | 0.1 | 35 | 25834 |
| 10 | 7.9 | 6.7 | 5.1 | 3.5 | 2.0 | 0.7 | 0.1 | 35 | 26760 |
| 11 | 11.1 | 8.9 | 6.2 | 3.6 | 1.3 | 0.2 | 0.1 | 35 | 22019 |
| 12 | 11.3 | 9.0 | 6.4 | 3.8 | 1.6 | 0.3 | 0.1 | 35 | 23231 |
| 13 | 8.1 | 6.7 | 5.0 | 3.3 | 1.7 | 0.5 | 0.1 | 35 | 25488 |
| 14 | 9.0 | 7.6 | 5.9 | 4.1 | 2.4 | 0.8 | 0.1 | 35 | 30932 |
| 15 | 8.8 | 7.6 | 6.0 | 4.4 | 2.7 | 1.1 | 0.1 | 35 | 31844 |
| 16 | 10.8 | 9.3 | 7.4 | 5.4 | 3.4 | 1.4 | 0.2 | 70 | 40097 |
| 17 | 9.4 | 7.8 | 5.9 | 3.9 | 1.9 | 0.6 | 0.1 | 35 | 28740 |
| 18 | 10.9 | 9.2 | 7.1 | 4.8 | 2.6 | 0.8 | 0.2 | 35 | 30265 |
| 19 | 11.6 | 10.0 | 7.9 | 5.6 | 3.2 | 1.1 | 0.2 | 35 | 31362 |
| 20 | 9.7 | 8.2 | 6.5 | 4.6 | 2.8 | 1.2 | 0.2 | 35 | 28691 |
| 21 | 10.0 | 8.7 | 7.1 | 5.4 | 3.6 | 1.9 | 0.6 | 280 | 73301 |
| 22 | 12.4 | 11.0 | 9.3 | 7.4 | 5.4 | 3.3 | 1.4 | 350 | — |
| 23 | 16.5 | 15.3 | 13.6 | 11.7 | 9.5 | 6.8 | 3.9 | 350 | — |
| 24 | 16.4 | 15.4 | 13.9 | 12.2 | 10.1 | 7.6 | 4.7 | 350 | — |
| 25 | 8.5 | 6.9 | 5.2 | 3.5 | 1.8 | 0.5 | 0.1 | 35 | 26688 |
| 26 | 9.3 | 7.2 | 4.8 | 2.5 | 0.6 | 0.1 | 0.0 | 35 | 21735 |
| 27 | 12.5 | 10.1 | 7.3 | 4.4 | 1.6 | 0.2 | 0.1 | 35 | 25437 |
| 28 | 13.9 | 11.5 | 8.6 | 5.5 | 2.4 | 0.4 | 0.1 | 35 | 31358 |
| 29 | 14.8 | 12.5 | 9.7 | 6.7 | 3.4 | 0.8 | 0.1 | 35 | 28568 |
| 30 | 12.5 | 10.1 | 7.4 | 4.6 | 2.0 | 0.4 | 0.1 | 35 | 24761 |
| 31 | 13.5 | 11.3 | 8.7 | 5.9 | 3.2 | 0.9 | 0.2 | 35 | 33336 |
| 32 | 13.9 | 12.0 | 9.6 | 7.1 | 4.4 | 1.8 | 0.4 | 245 | 75737 |
| 33 | 12.2 | 10.0 | 7.5 | 4.9 | 2.4 | 0.6 | 0.2 | 35 | 24184 |
| 34 | 14.2 | 12.0 | 9.3 | 6.5 | 3.8 | 1.4 | 0.4 | 140 | 51610 |
| 35 | 15.1 | 13.1 | 10.6 | 8.1 | 5.4 | 2.8 | 1.0 | 350 | — |
| 36 | 18.8 | 17.1 | 14.9 | 12.4 | 9.7 | 6.7 | 3.5 | 350 | — |
| 37 | 18.7 | 17.2 | 15.3 | 13.2 | 10.8 | 8.0 | 4.9 | 350 | — |
| 41 | 11.2 | 8.6 | 5.8 | 2.9 | 0.7 | 0.1 | 0.0 | 35 | 20968 |
| 42 | 10.3 | 8.2 | 6.0 | 3.8 | 1.8 | 0.4 | 0.1 | 35 | 25248 |

Figure 2:
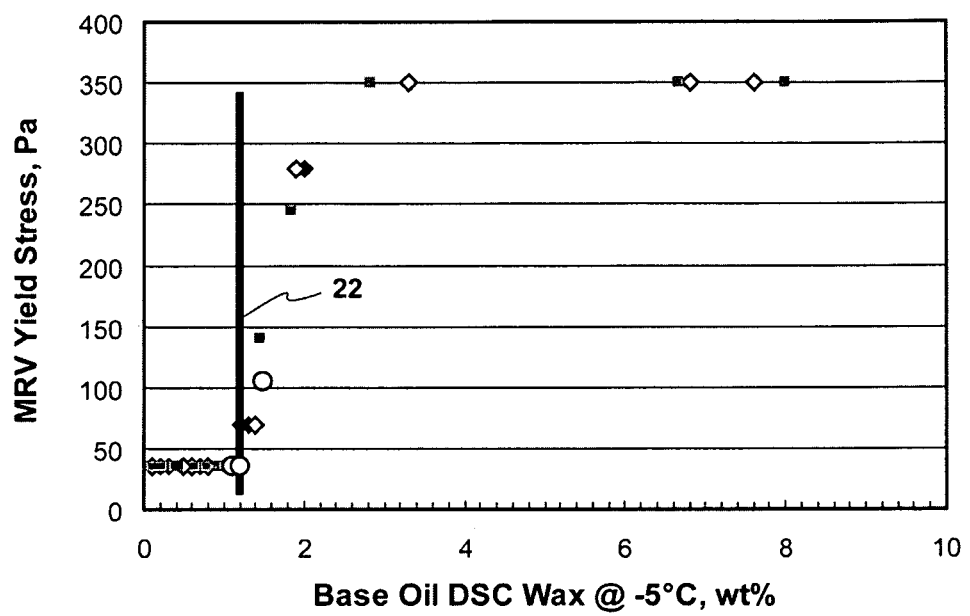
FIG. 2 is a graph illustrating the MRV yield stress for a 20W-50 automotive engine oil formulation versus base oil DSC Wax Content.

FIG. 2 shows the yield stress for the 20W-50 formulation versus the DSC wax content of the 600N base oils used in the formulation. FIG. 2 shows a yield stress pass/fail boundary 22. This boundary 22 is at about 1.2 wt % wax in base the base oil. The rapid increase in the yield stress of the finished oil when the 600N wax content is greater than 1.2 wt % suggests a critical concentration of wax as measured by the DSC technique which is needed to initiate the formation of a wax network structure in the finished oil. The wax network structure which is formed as the finished oil is cooled leads to the higher yield stress value in the MRV measurement.

Table 4 lists the MRV yield stress values and apparent viscosities at −20° C. for 10W-40 QA formulations using 150N base oil. Table 4 also lists the corresponding DSC data. For this viscosity grade, the MRV is limited by apparent viscosity rather than yield stress as was the case for the 20W-50 product.

TABLE 4

| Base stocks | DSC wax at −30 C. wt % | DSC wax at −25 C. wt % | DSC wax at −20 C. wt % | DSC wax at −15 C. wt % | DSC wax at −10 C. wt % | MRV yield stress at −30° C. Pa | MRV apparent visc at −30° C., cP |
|---|---|---|---|---|---|---|---|
| A | 8.7 | 6.4 | 4.2 | 2.2 | 0.5 | 35 | 27564 |
| B | 10.5 | 8.0 | 5.4 | 3.0 | 1.0 | 35 | 43634 |
| C | 10.5 | 8.0 | 5.4 | 3.0 | 1.0 | 35 | 42008 |
| D | 11.7 | 9.1 | 6.4 | 3.8 | 1.5 | 70 | 69801 |
| E | 11.7 | 8.9 | 6.0 | 3.3 | 0.9 | 35 | 53523 |
| F | 12.5 | 9.8 | 7.0 | 4.1 | 1.6 | 175 | 149468 |
| G | 9.3 | 7.0 | 4.7 | 2.5 | 0.6 | 35 | 29741 |
| H | 10.8 | 8.1 | 5.4 | 2.7 | 0.6 | 140 | 96406 |
| I | 10.4 | 7.8 | 5.1 | 2.6 | 0.5 | 175 | 164374 |
| J | 12.0 | 9.3 | 6.3 | 3.4 | 0.8 | 350 | 309818 |
| K | 12.5 | 9.6 | 6.6 | 3.6 | 1.0 | 280 | 240858 |
| L | 10.5 | 7.9 | 5.1 | 2.5 | 0.4 | 175 | 164968 |
| M | 9.5 | 7.1 | 4.7 | 2.5 | 0.6 | 35 | 43295 |
| N | 4.0 | 2.7 | 1.5 | 0.4 | 0.0 | 35 | 16521 |
| O | 5.6 | 4.0 | 2.4 | 1.0 | 0.1 | 35 | 18953 |

TABLE 4-continued

| Base stocks | DSC wax at −30 C. wt % | DSC wax at −25 C. wt % | DSC wax at −20 C. wt % | DSC wax at −15 C. wt % | DSC wax at −10 C. wt % | MRV yield stress at −30° C., Pa | MRV apparent visc at −30° C., cP |
|---|---|---|---|---|---|---|---|
| P | 7.7 | 5.8 | 3.8 | 2.0 | 0.4 | 35 | 23385 |
| Q | 5.9 | 4.3 | 2.5 | 1.0 | 0.1 | 35 | 19926 |
| R | 8.1 | 5.9 | 3.8 | 1.9 | 0.3 | 35 | 25891 |

Figure 3:
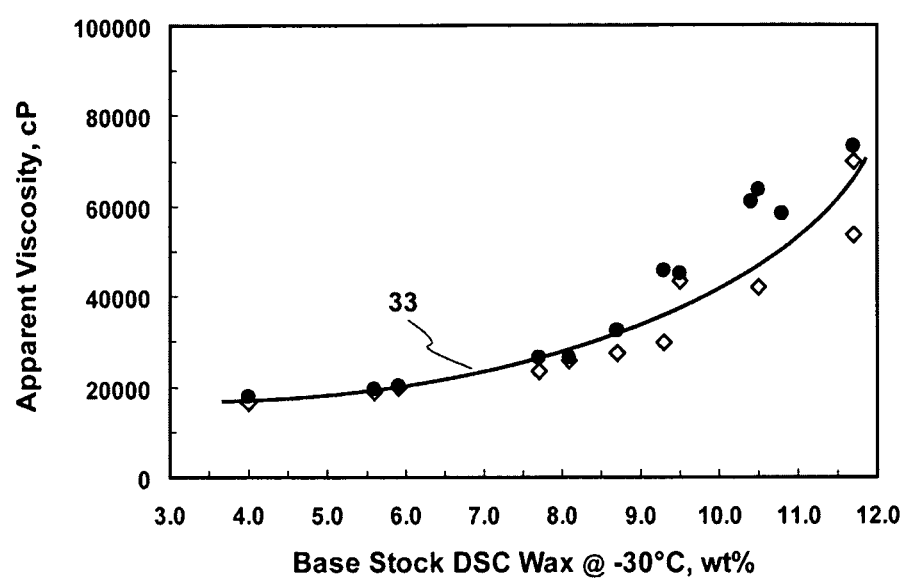
FIG. 3 is a graph illustrating the MRV apparent viscosity for a 10W-40 automotive engine oil formulation versus base oil DSC wax content.

FIG. 3 shows the MRV apparent viscosity as a function of DSC wax content at −30° C. for 150 N 10W-40 QA formulations. As shown in FIG. 3, a profile line 33 illustrates the relationship between wax content and apparent viscosity. The 10W-40 apparent viscosity limit for this particular formulation of 53,400 cP is reached at a base oil DSC wax content of about 11 wt %. It is this limiting value that sets the upper bound on the candidate crude approval within the CLFA protocol. Those skilled in the art will recognize that the DSC pass/fail boundary is dependent upon the specific formulation technology employed.

Figure 4:
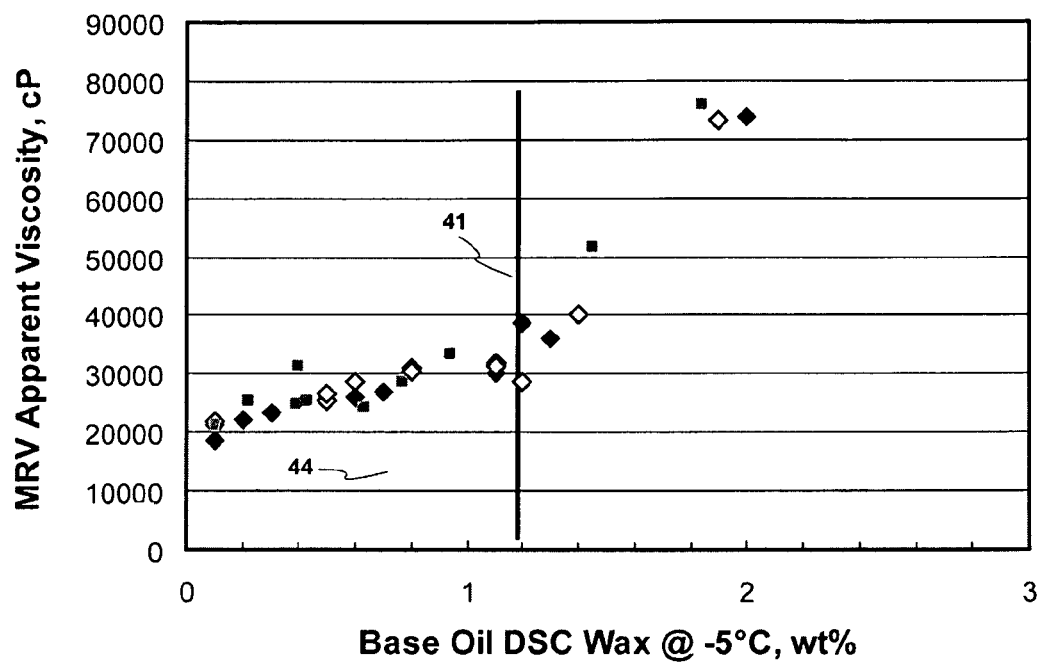
FIG. 4 is a graph illustrating the MRV apparent viscosity for 20W-50 automotive engine oil formulation versus base oil DSC Wax Content.

FIG. 4 is a graph illustrating apparent viscosity for 20W-50 formulation versus base oil DSC Wax Content. As shown in FIG. 4, the yield stress pass/fail boundary 43 is at 1.2 wt % wax 41 in base oil and corresponds to apparent viscosity of about 34,000 cP.

What is claimed is:

1. A method to determine at least one low temperature property of a lubricant oil comprising
   a. obtaining a base stock;
   b. generating a Differential Scanning Calorimetry (DSC) curve using a Differential Scanning Calorimeter of wax melting versus temperature and wax crystallization versus temperature for the base stock;
   c. converting the DSC curve of wax melting versus temperature to a wax amount versus temperature curve using the heats of fusion of the waxes contained in the base stock;
   d. calculating total wax level between two temperatures by integrating the wax amount versus temperature curve between the two temperatures;
   e. determining a Mini-Rotary Viscometer (MRV) value of a finished lubricant oil blended from the base stock using a predetermined empirical correlation of total wax level versus MRV; and
   f. using the determined MRV value to determine whether or not the corresponding fully formulated lubricant oil will pass MRV yield stress and apparent viscosity specifications.

2. The method of claim 1 wherein the DSC curve is generated comprising the steps of:
   a. heating up the base stock to a temperature of 80° C. to melt any wax structures in the base stock;
   b. cooling down the base stock to temperature between −50° C. to −80° C. at a cooling rate of 0.5° C. to 20° C. per minute to create a solid phase in the base stock; and
   c. heating the base stock at a heating rate of 5° C. to 20° C. per minute to determine wax melting versus temperature caused by the phase transition of the wax.

* * * * *